US008657483B2

(12) United States Patent
Nebergall et al.

(10) Patent No.: US 8,657,483 B2
(45) Date of Patent: Feb. 25, 2014

(54) APPARATUSES FOR DILUTE PHASE IMPREGNATION OF A MILLED SORBENT WITH A CHEMICAL COMPOUND IN AN AQUEOUS SOLUTION

(75) Inventors: Robert S. Nebergall, Longview, TX (US); Patton M. Adams, Longview, TX (US)

(73) Assignee: Cabot Norit Americas, Inc., Marshall, TX (US)

( * ) Notice: Subject to any disclaimer, the term of this patent is extended or adjusted under 35 U.S.C. 154(b) by 190 days.

(21) Appl. No.: 12/875,195

(22) Filed: Sep. 3, 2010

(65) Prior Publication Data

US 2012/0058885 A1    Mar. 8, 2012

(51) Int. Cl.
*B01F 5/04*   (2006.01)
*B01F 5/18*   (2006.01)

(52) U.S. Cl.
USPC ..................................... 366/173.1

(58) Field of Classification Search
USPC ............. 366/101, 137.1, 162.4, 167.1, 366/173.1–173.2, 174.1, 175.2, 181.5
See application file for complete search history.

(56) References Cited

U.S. PATENT DOCUMENTS

| 722,310 | A | * | 3/1903 | Lapp ........................... 366/169.1 |
| 1,788,466 | A | | 1/1931 | Lourens |
| 3,207,824 | A | * | 9/1965 | Wurster et al. ............... 264/117 |
| 3,794,299 | A | * | 2/1974 | Wagner et al. ............. 210/198.1 |
| 4,323,314 | A | | 4/1982 | Kaiser-Wirz |
| 4,474,477 | A | | 10/1984 | Smith et al. |
| 4,578,876 | A | | 4/1986 | Cartwright et al. |
| 4,848,673 | A | | 7/1989 | Masuda et al. |
| 5,053,279 | A | | 10/1991 | Daniels et al. |
| 5,470,893 | A | | 11/1995 | Sinclair-Day et al. |
| 5,626,422 | A | * | 5/1997 | Adamo et al. ............. 366/173.1 |

(Continued)

FOREIGN PATENT DOCUMENTS

GB    2 122 916 A    1/1984

OTHER PUBLICATIONS

PCT Notification of Transmittal of the International Search Report and the Written Opinion of the International Searching Authority, or the Declaration with attached PCT International Report and the Written Opinion of the International Searching Authority in International Application No. PCT/US2011/049056, dated May 21, 2012, 17 pages.

*Primary Examiner* — Charles E Cooley

(57) ABSTRACT

The present disclosure relates to apparatus designed to impregnate a sorbent. In some embodiments apparatus of the disclosure may comprise a mixing vessel having either a conical mixing chamber or an cylindrical mixing chamber designed to increase the contact surface area and/or contact/residence time of a sorbent and impregnant to produce compositions comprising an impregnated sorbent. Apparatus of the disclosure may also comprise one or more atomizers operable to produce atomized droplets of impregnant. The disclosure also provides methods for impregnation of a milled sorbent or an un-milled sorbent. Methods of the disclosure provide several technical advantages and may be cost effective. Impregnant sorbent compositions produced by methods and/or apparatus of the disclosure may have higher concentrations of an impregnant, a more uniform distribution of an impregnant and may have a greater sorbent efficiency.

5 Claims, 9 Drawing Sheets

(56) References Cited

U.S. PATENT DOCUMENTS

| | | |
|---|---|---|
| 6,143,057 A | 11/2000 | Bülow et al. |
| 6,186,658 B1 * | 2/2001 | Nishida et al. ............ 366/173.2 |
| 7,611,756 B2 * | 11/2009 | Pfeifer et al. ................. 427/533 |
| 7,815,864 B2 | 10/2010 | Betz et al. |
| 2001/0002387 A1 | 5/2001 | Tsutsumi et al. |
| 2003/0007911 A1 | 1/2003 | Le Claire et al. |
| 2006/0293194 A1 | 12/2006 | Hajmrle et al. |
| 2008/0283446 A1 | 11/2008 | Tatarchuk et al. |
| 2008/0305447 A1 | 12/2008 | Wheeler et al. |
| 2012/0058885 A1 * | 3/2012 | Nebergall et al. ............ 118/612 |

* cited by examiner

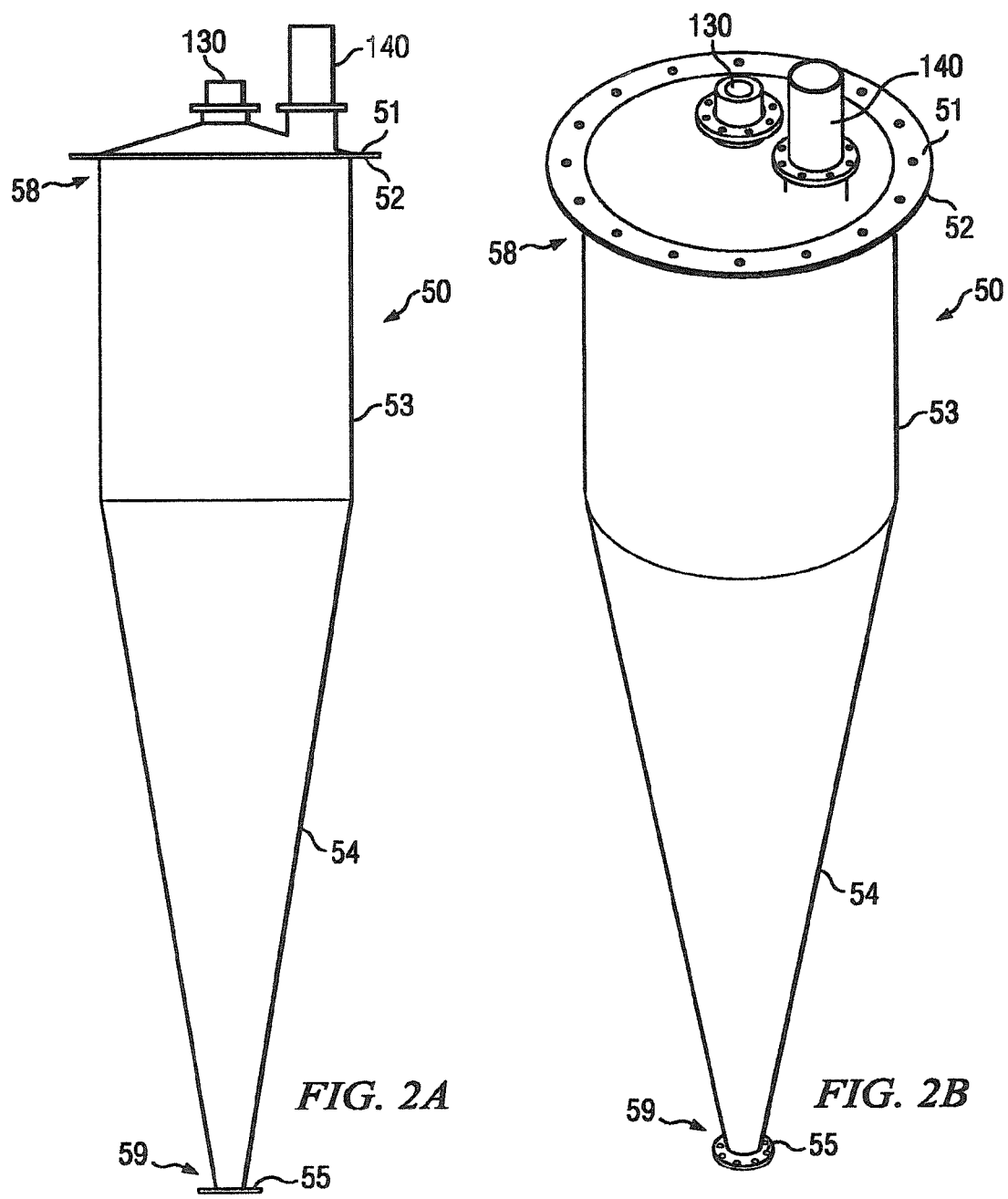
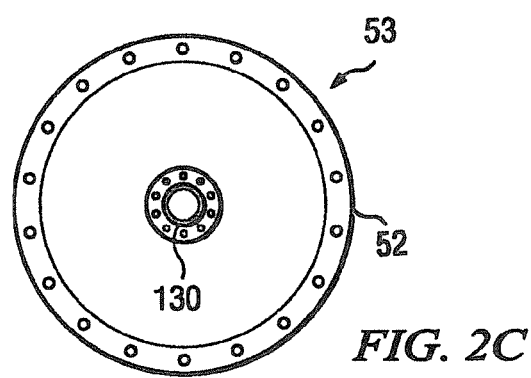
FIG. 2A  FIG. 2B  FIG. 2C

APPARATUSES FOR DILUTE PHASE IMPREGNATION OF A MILLED SORBENT WITH A CHEMICAL COMPOUND IN AN AQUEOUS SOLUTION

TECHNICAL FIELD

The present disclosure relates to methods for impregnating a sorbent with an impregnant and to compositions comprising at least one sorbent (e.g., a milled sorbent, non-milled sorbent, activated carbon, non-carbon sorbents) and an impregnant (e.g., a halogen). In some embodiments, the disclosure relates to apparatuses and devices designed for impregnating a sorbent and/or for making compositions of the disclosure.

BACKGROUND OF THE INVENTION

Contaminants, such as mercury, may be removed from flue gases and from exhaust emitted from power plants by halogenated activated carbon sorbents and non-carbon sorbents. Methods to make halogenated activated carbon comprise halogenating an activated carbon sorbent and milling the halogenated activated carbon.

Halogens are typically in an aqueous solution during the halogenation process and/or milling process. Aqueous halogen solutions are corrosive and corrode moving parts of mills used to mill halogenated activated carbons. This adversely affects milling operations. For example, corroded mill parts do not function well and repeated replacements and maintenance issues slow down production. The effects on milling operations result in high costs associated with part replacement and time lost to shutting down of production lines for repair or maintenance.

In addition, present methods of making halogenated activated carbon sorbents do not produce uniformly halogenated sorbents. This greatly affects the contaminant removal efficiency of the halogenated sorbents.

SUMMARY

The present disclosure, in some embodiments relates to methods and apparatuses designed to impregnate sorbents.

Apparatus of the disclosure, according to some embodiments, may be designed to increase the contact surface area and/or contact/residence time of a sorbent and an impregnant to produce compositions comprising an impregnated sorbent.

In one embodiment, an apparatus of the disclosure may comprise a mixing vessel having a conical chamber designed to generate a turbulent formation of inflowing sorbent particles. The conical chamber may also have at least one atomizer disposed therein that is operable to produce atomized droplets of impregnant. In some embodiments, turbulent mixing of atomized impregnant droplets with particles of sorbent flowing in a turbulent formation may result in a greater contact time and/or expose greater surface area of sorbent and impregnant to each other thereby producing impregnant sorbent having a substantially uniform impregnant distribution and a substantially high impregnant incorporation into a sorbent.

In some embodiments, an apparatus of the disclosure may comprise a mixing vessel having a cylindrical vessel, also referred to as an impregnation cylinder, and may have one or more atomizers disposed therein. The impregnation cylinder may be designed to generate a turbulent formation of inflowing sorbent particles. Atomized droplets of impregnant may be sprayed onto the turbulent flow of sorbent at multiple points allowing contact and mixing of sorbent and impregnant droplets.

In some embodiments, components of an apparatus may comprise devices and/or software to synchronize one or more steps, regulate reaction conditions and/or perform an operation cycle.

In some embodiments, methods for impregnation of a milled sorbent are described and may comprise contacting a milled sorbent with an impregnant to allow maximum surface area of a milled sorbent to be contacted with impregnant. Methods of the disclosure may result in an increased residence time of reactants.

In some embodiments, methods for impregnation of an un-milled sorbent are described and may comprise contacting a sorbent that is not milled with atomized droplets of an impregnant. In some embodiments, turbulent mixing of sorbent and impregnant increase surface area contact as well as increase residence time. Methods of the disclosure may provide several technical advantages and may be cost effective.

The disclosure also describes impregnant sorbent compositions produced by methods and/or apparatus of the disclosure. In some embodiments, compositions of the disclosure may have higher concentrations of an impregnant, a more uniform distribution of an impregnant and/or may have a greater sorbent efficiency.

Some embodiments of the disclosure may provide one or more of the following technical advantages. A technical advantage of some embodiments may include uniform impregnation of a milled sorbent with an impregnant. Additionally, an increase in efficiency of contaminant removal (e.g., mercury removal) by an impregnated milled sorbent made by a method of the present disclosure may occur. Another technical advantage of some embodiments may include elimination or reduction of damage by aqueous halogens to mill components. Therefore, time and costs associated with replacement of mill parts and maintenance of milling operations may be reduced. Some embodiments may also increase milling capacity and throughput, which also results in cost savings. Yet another technical advantage of some embodiments may include elimination of cross contamination of a mill by a halogen or other impregnant. Therefore, a mill may be used for multiple processes because halogen contaminants do not contact mill parts.

A technical advantage of some embodiments may be a continuous process that may be efficient, consistent and less expensive for impregnating a milled sorbent. The adsorption of impregnant and/or the increased evaporation of moisture may be increased by a milled sorbent. Additionally, a decrease in caking and plugging of mill parts by impregnated sorbent may occur. A technical advantage of certain embodiments may also include an increase in flowability of the impregnated sorbent.

Various embodiments of the disclosure may include none, some, or all of the above technical advantages. One or more other technical advantages may be readily apparent to one skilled in the art from the figures, descriptions, and claims included herein.

BRIEF DESCRIPTION OF THE DRAWINGS

For a more complete understanding of the present disclosure, its features and advantages, reference is now made to the following description, taken in conjunction with the accompanying drawings, in which:

FIG. 1 illustrates an exemplary apparatus operable to impregnate a sorbent having a mixing vessel comprising a conical mixing chamber, according to one example embodiment;

FIG. 2A illustrates a mixing vessel having a conical mixing chamber, according to one example embodiment;

FIG. 2B illustrates a top-view of a mixing vessel having a conical mixing chamber, according to one example embodiment;

FIG. 2C depicts an example flange comprised in a mixing vessel having a conical mixing chamber, according to one example embodiment;

DETAILED DESCRIPTION

It should be understood at the outset that, although example implementations of embodiments of the disclosure are illustrated below, embodiments of the present disclosure may be implemented using any number of techniques, whether currently known or not. The present disclosure should in no way be limited to the example implementations, drawings, and techniques illustrated below. Some embodiments of the disclosure and associated advantages may be best understood by reference to FIGS. 1-8 wherein like numbers refer to same and like parts.

The present disclosure, in some embodiments, relates to methods and apparatuses and/or devices for making impregnated sorbent compositions that may be used to decontaminate fluids. Compositions of the disclosure, i.e., impregnated sorbents, may be operable to remove, lower, and/or reduce contaminants, hazardous materials and/or pollutants such as mercury, fly ash, acid gases, dioxins, furans, mercury-containing compounds, heavy metal compounds, biological toxins from other polluted/contaminated fluids such as industrial fluids, exhaust gases, power plant emissions, contaminated blood or other biological fluids.

Figure 1:
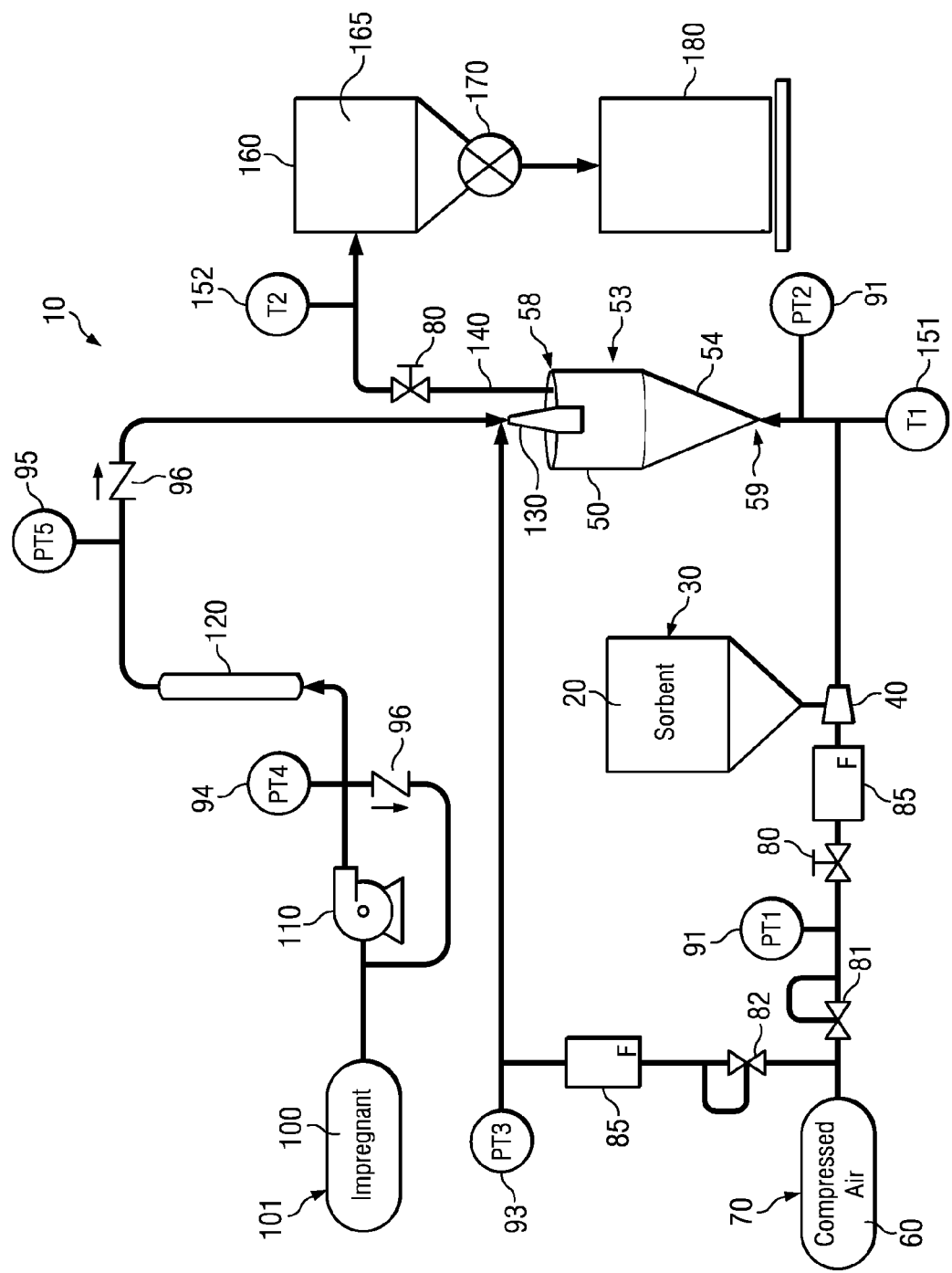

In some embodiments, the disclosure provides apparatuses designed to impregnate a sorbent. FIG. 1 illustrates a process flow diagram showing an apparatus 10 comprising a mixing vessel 50 having a conical mixing chamber operable to impregnate sorbent 20 from an impregnated sorbent 165, according to one example embodiment.

Sorbent 20 may include any sorbent that may be used for decontamination applications and may comprise any material operable to adsorb and/or chemically bind to a hazardous molecule or a contaminant molecule to remove, reduce, or lower the level of the hazardous molecule or the contaminant molecule. In some embodiments, sorbent 20 may be a milled sorbent. Milling a sorbent greatly increases it surface area thereby allowing for greater capacity for adsorbing a hazardous molecule or a contaminant. While several example embodiments are described herein with regard to milled and/or powdered sorbent 20, teachings recognize that the present disclosure is not limited to milled sorbents. Accordingly, sorbents that are not milled or powdered may also be impregnated using the methods and apparatus described herein. For example, in some embodiments, sorbents that are not milled or powdered but have a particle size of from about 10 microns to 30 microns ($10\mu$ to $30\mu$) may be impregnated by the present methods and devices. In some embodiments, any sorbent having the ability to fluidize with air to a turbulent velocity may be used.

Apparatus 10 as shown in FIG. 1 may comprise sorbent delivery chamber 30 (also referred to as a sorbent feeder, a silo or a delivery chute) having sorbent 20. Sorbent delivery chamber 30 represents a device to deliver sorbent 20 to an impregnation chamber, such as mixing vessel 50 having a conical mixing chamber.

From sorbent delivery chamber 30, sorbent 20 may be delivered or fed into bottom end 59 of mixing vessel 50 having a conical mixing chamber via pump 40 as a dilute phase sorbent with compressed air or low pressure air 60. A dilute phase sorbent conveying refers to a solid or a sorbent conveyed by a gas where the gas velocity exceeds the saltation velocity.

40 represents a pump that is operable to transfer energy from one fluid to another. In some embodiments, 40 may be an eductor or a jet-pump. Pressure valve 91 may regulate the flow. Component 151 may comprise a thermocouple to measure temperature of the gas entering mixing vessel 50.

Mixing vessel 50 having a conical mixing chamber (also referred to herein as cone 50) is a cone shaped vessel having a first end or top end 58 and a second end or bottom end 59. Mixing vessel 50 having a conical mixing chamber may be lined and/or comprised of a corrosion resistant and temperature transfer resistant material. Mixing vessel 50 having a conical mixing chamber may be made from a variety of material including non-limiting examples such as stainless steel, dual composite material comprising polyvinyl chloride (PVC), reinforced polyester or others. In some embodiments, the core of mixing vessel 50 having a conical mixing chamber may comprise stainless steel. The size and height of the walls of mixing vessel 50 having a conical mixing chamber may be designed to maintain sorbent 20 in a dilute phase.

Mixing vessel 50 having a conical mixing chamber may have a top portion 53 that is a cylindrical chamber (also called a top chamber) and a bottom portion 54 that is a conical chamber (also called a bottom chamber). Atomizer 130 may be disposed toward top end 58 of mixing vessel 50 having a conical mixing chamber. In some embodiments, mixing vessel 50 having a conical mixing chamber may comprise multiple atomizers (not expressly depicted). Product discharge tube 140 may be disposed toward top end 58 of mixing vessel 50 having a conical mixing chamber. Product discharge tube 140 may also be referred to variously as discharge tube or discharge chute.

The shape of mixing vessel 50 having a conical mixing chamber may be designed to allow for turbulence formation in bottom portion 54 of vessel 50 following the flow of sorbent 20 and compressed air 60 through second end 59. In some embodiments, mixing vessel 50 having a conical mixing chamber may be designed to generate a turbulence formation having flow and dynamics for efficient mixing of milled or non-milled sorbent 20 with atomized droplets of impregnant 100. In some embodiments, construction of mixing vessel 50 having a conical mixing chamber with temperature transfer resistant material may be designed to facilitate maintenance of the temperature of a reaction in cone 50 within a range where impregnant 100 remains in an aqueous phase and is not converted into a gaseous phase.

Mixing vessel 50 having a conical mixing chamber may also be designed to have a reverse flow for discharging impregnated sorbent 165 via product discharge tube 140 out of cone 50. The shape of mixing vessel 50 having a conical mixing chamber may be operable to reduce or prevent caking and plugging of outlets and inlets by components of the reaction or by a product. In some embodiments, maintenance of turbulent velocity during the formation and drafting may reduce or prevent caking or plugging. Other embodiments relating to mixing vessel 50 having a conical mixing chamber are described in sections below and in FIGS. 2A-2G.

Apparatus 10 may also comprise compressed air source 70 having compressed air 60 operable to be delivered (or fed) with sorbent 20 into bottom end 59 of mixing vessel 50 having a conical mixing chamber via regulator 81, pressure valve 91, valve 80, element 85 and through eductor 40.

In non-limiting examples, compressed air source 70 may be an air cylinder having air under high pressure (e.g., a high pressure air compressor), air under low pressure or a blower. In some embodiments, compressed air 60 may be at a pressure of about 90 ACFM to about 900 ACFM. Compressed air 60 may comprise oxygen, nitrogen, or combinations thereof.

Compressed air source 70 may also supply compressed air 60 to atomizer 130 located at top end 58 of mixing vessel 50 having a conical mixing chamber. Regulator 82, air flow meter 85 and pressure valve 93 may control the flow of compressed air to atomizer 130.

Impregnant 100 may be contained in container 101 and fed via pump 110 into atomizer 130. Rotameter 120 measures the flow rate of impregnant 100, and pressure valves 94 and 95 and element 96 regulate the flow of impregnant 100 and compressed air 60 into atomizer 130.

Atomizer 130 may be operable to atomize impregnant 100 into atomized droplets (not expressly shown). In some embodiments, atomizer 130 may be operable to atomize impregnant 100 into atomized droplets that are similar in size to the size of milled sorbent 20. In some embodiments, atomizer 130 may be operable to atomize impregnant 100 into droplets having a size range of about 10μ to about 30μ. However, teachings recognize that atomized droplets of other sizes may be used as well and the present disclosure is not limited to droplets in the size range of 10μ to 30μ. In some embodiments, more than one atomizer 130 may be used (not expressly depicted).

Atomizer 130 may be operable to spray atomized aqueous impregnant at an angle of 10° to 15° relative to the turbulent flow of sorbent 20. The angle of spray of atomizer 130 may be broad enough to distribute impregnant 100 to substantially all particles of sorbent 20. The angle of the atomizer spray may also be designed to avoid spraying the exiting product 165.

An impregnated sorbent 165, product 165, may exit mixing vessel 50 having a conical mixing chamber through product discharge tube 140. Product discharge tube 140 may be attached to collection chamber 160 where impregnated milled sorbent 165 (product 165) may be collected following impregnation in mixing vessel 50 having a conical mixing chamber. Regulatory valve 80 may control the flow of product 165 into collection chamber 160 (also referred to as dust collector). Thermocouple 152 may measure exit temperature following impregnant adsorption for impregnant into sorbent. Rotary valve 170 may control the flow of impregnated sorbent 165 into chamber 180. Dust collector 160 (also referred to as collection chamber) may separate air and impregnated sorbent. Dust collector 160 may have filters, such as but not limited to filter bags, to separate air and impregnated sorbent. Dust collector 160 may also have a blower. Chamber 180 may be a storage container or a bulk bag to collect and/or store impregnated sorbent 165.

Apparatus 10 may also comprise one or more computers, one or more process control programs, one or more data input programs, and/or one or more data output readers (not expressly shown). In some embodiments, apparatus 10 may be started and shut-down automatically by an automated process control program. In some embodiments, apparatus 10 may be started, shut down and controlled in intermediate steps manually. In some embodiments, apparatus 10 may be started, shut-sown and controlled in intermediate steps by a combination of automated and manual steps. Manual control may be by human operators.

Automated controls, manual controls and/or combinations thereof may be used for maintenance operations. Maintenance operations may include washing one or more components of apparatus 10.

Automated controls may also be used for one or more of the following including: synchronization of input of sorbent and compressed air, synchronization of input of aqueous impregnant and compressed air for atomization, controlling residence time in the apparatus cone (or mixing vessel 190 comprising a cylindrical mixing chamber as described later), and exiting of impregnated product.

In an exemplary embodiment, sorbent 20 flows through apparatus 10 to form an impregnated sorbent 165 in mixing vessel 50 having a conical mixing chamber. Teachings of the disclosure may be used to impregnate any sorbent 20 with any impregnant 100. Exemplary sorbent 20 that may be impregnated by methods of the disclosure using apparatus 10 comprising mixing vessel 50 having a conical mixing chamber (and/or mixing vessel 190 comprising a cylindrical mixing chamber as described later) may comprise an activated carbon sorbent such as a lignite, a brown coal, an activated carbon having an average diameter of less than about 40μ, a powdered activated carbon sorbent such as but not limited to a lignite, a brown coal, a powdered activated carbon having an average diameter of less than about 40μ, sorbents having an average diameter of from about 10μ to about 30μ, or any combinations thereof. A description of various activated carbon sources is provided below.

Impregnant 100 may be any chemical or biochemical agent that may be impregnated into sorbent 20. Impregnant 100 may be operable to increase adsorption efficiency of a sorbent for one or more contaminant. In some embodiments, impregnant 100 may be operable to chemically react with a contaminant and render it less toxic. Accordingly, impregnant 100, in some embodiments, may be operable to detoxify a decontaminant or a toxic agent. Impregnant 100 may have a high affinity for a contaminant and, in some embodiments, may further be operable to adsorb, chemically bind, capture, and/ or selectively bind a contaminant. Non-limiting examples of impregnants may include halogens, sulfur, silver, or cations, such as Al, Mn, Zn, Fe, Li, Ca. In some embodiments, impregnant 100 may comprise a halogen. Exemplary halogens in aqueous phase may include fluorine (F), chlorine (Cl), bromine (Br) and iodine (I). Example halogen impregnants of the disclosure may comprise salts such as but not limited to sodium (Na) or potassium (K), acids such as but not limited to hydrochloric acid (HCl), or bases. In some embodiments, impregnant 100 may be in an aqueous phase. An aqueous phase may comprise water. For example, in one example embodiment, an aqueous solution of sodium bromide (NaBr) may be used as an impregnant.

In one example embodiment, flow of sorbent 20, through apparatus 10, may begin with delivery of sorbent 20 from sorbent delivery chamber 30 into bottom end 59 of mixing vessel 50 having a conical mixing chamber. Delivery and flow of sorbent 20 into mixing vessel 50 having a conical mixing chamber may be facilitated by compressed air source 70 having compressed air 60. Accordingly, compressed air 60 and sorbent 20 may be delivered simultaneously into bottom end 59 of mixing vessel 50 having a conical mixing chamber and may be regulated by one or more of regulator 81, pressure valve 91, valve 80, and/or element 85 through eductor 40. Sorbent 20 and air 60 may comprise a dilute phase sorbent. In some embodiments, sorbent 20 may enter end 59 of mixing vessel 50 having a conical mixing chamber at a rate of from about 1000 lb/hr to about 5000 lb/hr.

Inflow of sorbent 20 simultaneously with compressed air 60 into conical chamber 54 of mixing vessel 50 having a conical mixing chamber results in a turbulence formation, or a turbulent flow, comprising particles of sorbent 20 having a turbulent velocity. As described earlier, the shape of mixing vessel 50 having a conical mixing chamber facilitates turbulence formation or turbulent flow in conical chamber 54.

At the same time, impregnant 100 may be delivered to top end 58 of mixing vessel 50 having a conical mixing chamber via atomizer 130. Delivery of impregnant 100 from container 101 into atomizer 130 may be facilitated by pump 110, pressure valves 94 and 95, rotameter 120, and element 96. Compressed air 60 from compressed air source 70 may be delivered into atomizer 130 simultaneously with impregnant 100. Compressed air 60 along with impregnant 100 enter atomizer 130 and may be atomized into atomized droplets of impregnant 100 as they enter top end 58 of mixing vessel 50 having a conical mixing chamber.

In some embodiments, a finer particle size of atomized droplets of impregnant 100 formed by atomizer 130 may result in a larger surface area of impregnant 100 operable to contact sorbent 20. In some embodiments, atomizer 130 may spray atomized impregnant 100 at an angle relative to the turbulent flow of sorbent 20. In some embodiments, the angle of spray of atomizer 130 may distribute impregnant to substantially all particles of sorbent 20. The angle of spray relative to the turbulent flow of sorbent may be but is not limited to 10° to 15°.

As atomized droplets of impregnant 100 flow in through atomizer 130 into first end 58 of cone 50, the atomized droplets come in contact with a turbulent formation comprising milled sorbent 20 and compressed air 60. This results in mixing sorbent 20 and impregnant 100 in cone 50. In some embodiments, the mixing may be turbulent mixing (i.e., mixing occurring at turbulent velocities of one or more of the components being mixed). Mixing results in adsorption of impregnant 100 into milled sorbent 20 and formation of impregnated sorbent 165.

In some embodiments, turbulence formation in mixing vessel 50 having a conical mixing chamber may have flow and dynamics for efficient mixing of sorbent 20 with atomized droplets of impregnant 100. In embodiments where non-milled sorbents 20 may be impregnated using cone 50 and/or other parts of apparatus 10, the particle size of non-milled sorbent 20 may be fine enough to fluidize with compressed air 60 at a respective velocity of turbulence to allow mixing of particles of non-milled sorbent 20 with impregnant 100.

Impregnated sorbent 165 may exit mixing vessel 50 having a conical mixing chamber by a reverse flow via product discharge tube 140. Product 165 may exit out by drafting through discharge tube 140 into dust collector chamber 160. A draft from dust collector blower (not expressly shown) may pull air/sorbent through toward dust collector chamber 165. Impregnated sorbent 165 may be forced out from mixing vessel 50 by the pressure difference between mixing vessel 50 and dust collector 160.

While the velocity of air and sorbent may vary inside mixing vessel 50 having a conical mixing chamber, the air and sorbent 20 remain in a turbulent regime. Once the gas/sorbent reaches discharge tube 140, the velocity increases significantly due to the pressure difference between the mixing vessel 50 and the dust collector 160. In response to the pressure difference, impregnated sorbent 165 and air may exit toward the top 58 of mixing vessel 50, in a dilute phase, via discharge chute 140 that extends down into the turbulent volume of mixing vessel 50.

The air may be drafted or pulled through filter bags located in dust collector 160 and discharged out of a blower (not shown). Impregnated sorbent 165 now separated from the air, falls to a bottom hopper in dust collector 160 and may be discharged to a storage container 180 via a rotary valve 170.

Milled sorbent 20 impregnated with impregnant 100, also referred to as impregnated adsorbent 165, made using apparatus 10 of the present disclosure, may have an increased efficiency for adsorbing and decontaminating a fluid (such as a flue gas or an exhaust gas) as compared to a milled sorbent 20 that is not impregnated. In some embodiments, impregnated adsorbent 165 may be operable to increase sorbent efficiency by detoxifying a contaminant or a hazardous molecule as compared to milled sorbent 20 that is not impregnated. In one example embodiment, an impregnated sorbent 165 may comprise impregnant 100 comprising a halogen and may be operable to oxidize mercury (Hg) from flue gases and exhaust gases.

FIG. 2A illustrates an exemplary mixing vessel 50 having a conical mixing chamber having a top end 58 and a second end 59. Atomizer 130 and product discharge tube 140 may be located toward top end 58.

FIG. 2B illustrates a top-view of mixing vessel 50 having a conical mixing chamber showing individual parts. In some embodiments, parts of mixing vessel 50 having a conical mixing chamber may be releasably attached.

FIG. 2C depicts an example flange 52 that couples to cylindrical chamber 53.

Figure 2D:
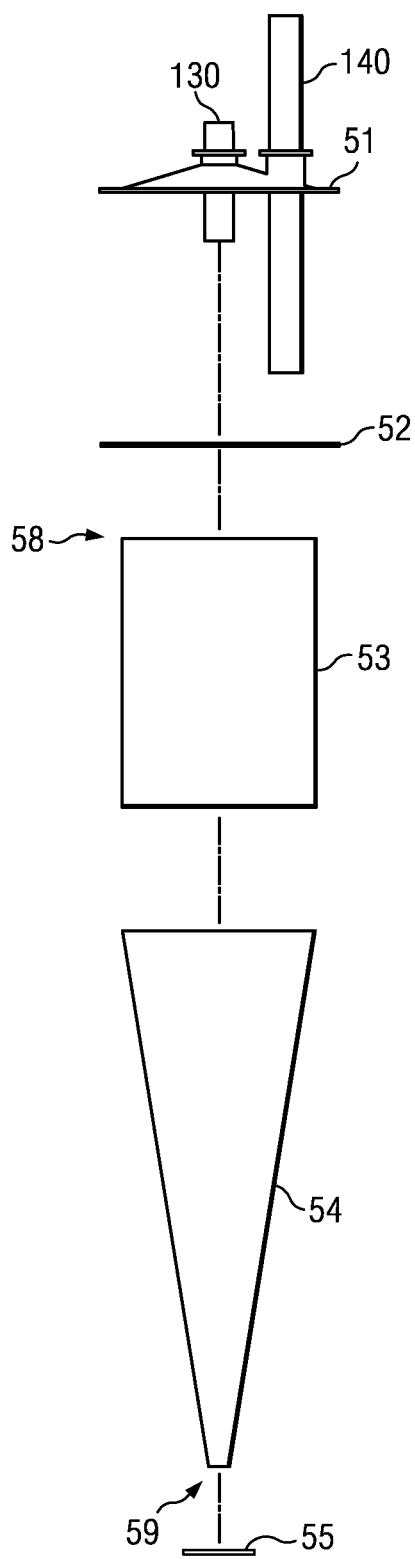
FIG. 2D illustrates different parts of a mixing vessel having a conical mixing chamber of FIG. 2A, according to one example embodiment.

FIG. 2D illustrates a two dimensional representation of different parts of mixing vessel 50 having a conical mixing chamber as described in FIG. 2A and shows top flange 51 having atomizer 130 and discharge chute 140 disposed therein, flange 52, cylindrical chamber 53, bottom conical chamber 54, and bottom flange 55. Flanges 51 and 52 may facilitate a seal between the various components.

Figure 2E:
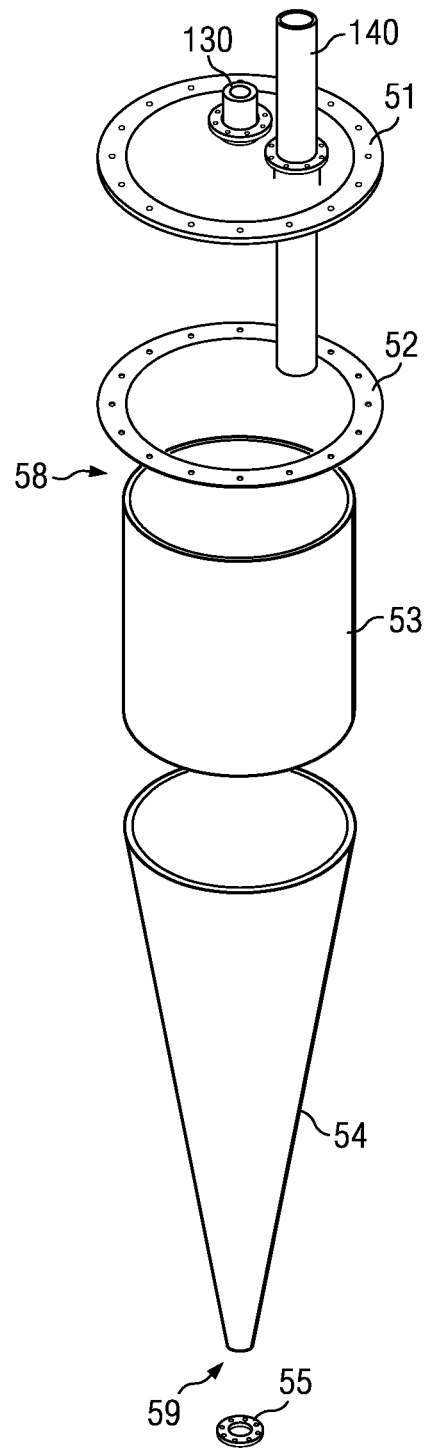
FIG. 2E illustrates a three dimensional view of different parts of a mixing vessel having a conical mixing chamber as shown in FIG. 2B, according to one example embodiment.

FIG. 2E illustrates a three-dimensional view of components of mixing vessel 50 having a conical mixing chamber as shown in FIG. 2B. Top flange 51 may be located toward top end 58 of cone 50. Atomizer 130 and product discharge tube 140 may be attached to top flange 51. Atomizer 130 and product discharge tube 140 may be disposed into various elements of flange 51. In other embodiments, atomizer 130 or discharge tube 40 may be located in different positions on flange 51.

Cylindrical chamber 53 and bottom conical chamber 54 are located below flange 52. Bottom flange 55 is located toward second end 59 of cone 50 and may be releasably attached to the body.

Figure 2F:
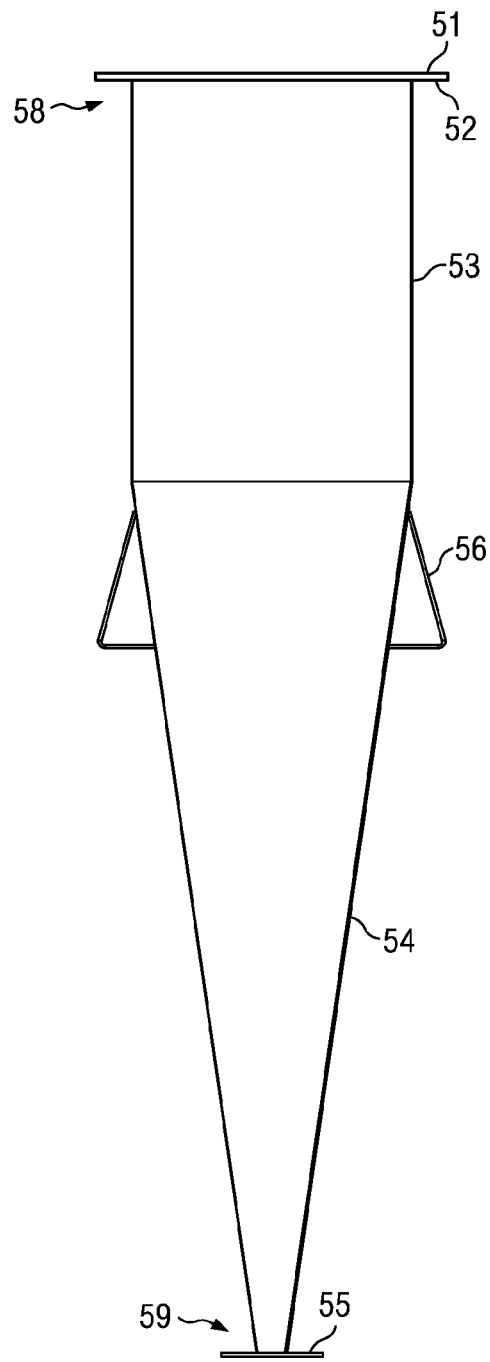
FIG. 2F illustrates a two-dimensional view of a mixing vessel having a conical mixing chamber showing handle 56, according to one example embodiment.
Figure 2G:
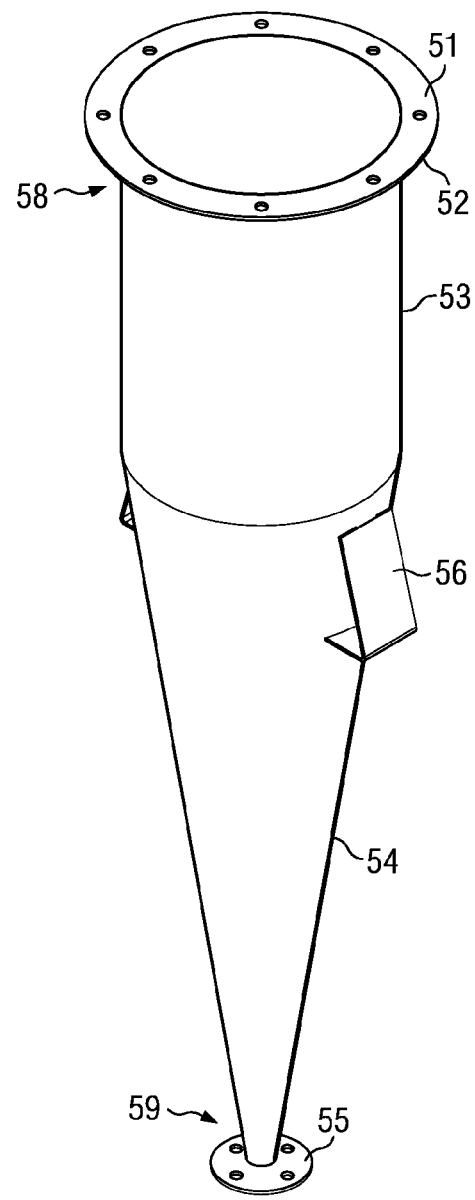
FIG. 2G illustrates a three-dimensional view of a mixing vessel having a conical mixing chamber as shown in FIG. 2F, according to one example embodiment.

FIG. 2F illustrates a two-dimensional view of an exemplary mixing vessel 50 having a conical mixing chamber showing handle 56. Handle 56 may be releasably attached to bottom conical chamber 54 to facilitate moving chamber 54. FIG. 2G illustrates a three dimensional view of mixing vessel 50 having a conical mixing chamber as shown in FIG. 2E.

Figure 3:
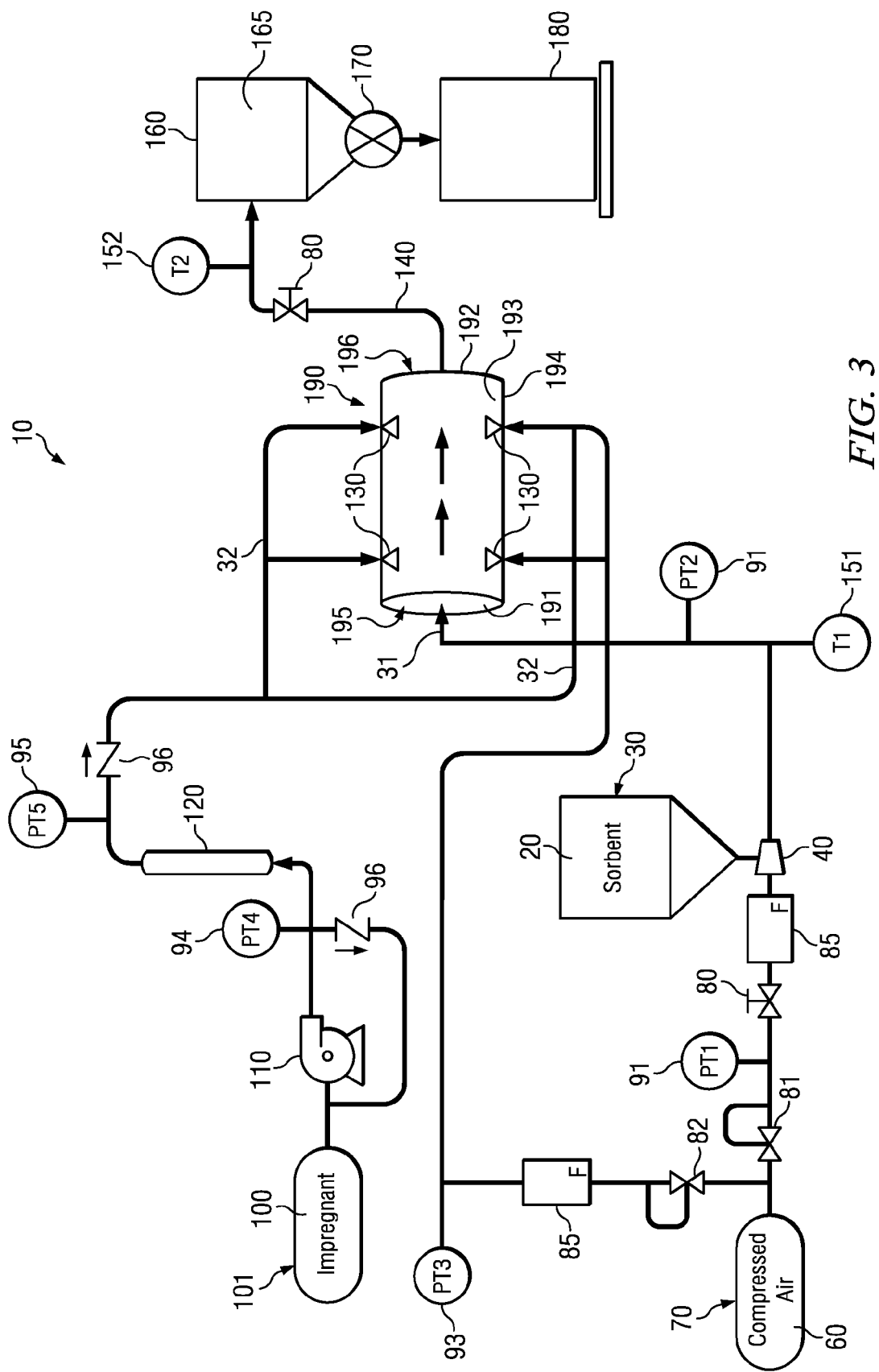
FIG. 3 illustrates an exemplary apparatus operable to impregnate a sorbent having a mixing vessel having a cylindrical mixing chamber, according to one example embodiment.

FIG. 3 illustrates another exemplary apparatus 10 having mixing vessel 190 comprising a cylindrical mixing chamber operable to impregnate sorbent 20. Several elements of apparatus 10 of FIG. 3 are similar to apparatus 10 described in FIG. 1, but sorbent 20 impregnation occurs in mixing vessel 190 comprising a cylindrical mixing chamber rather than in mixing vessel 50 having a conical mixing chamber.

Apparatus 10 as shown in FIG. 3 may comprise sorbent delivery chamber 30 having sorbent 20. Sorbent delivery chamber 30 represents a device to deliver sorbent 20 into mixing vessel 190 comprising a cylindrical mixing chamber.

Mixing vessel 190 comprising a cylindrical mixing chamber (also referred to herein as cylinder 190) comprises a cylindrical vessel having a first end 191 and a second end 192. A first flange 195 may be disposed on first end 191. Flange 195 may have inlet 31 for entry of sorbent 20 and compressed air 60 into cylinder 190. A second flange 196 may be disposed on second end 192. Flange 192 may include outlet 140, also described as product discharge tube 140, to discharge impregnated sorbent 165 from cylinder 190.

Cylindrical mixing chamber of mixing vessel 190 may have an external surface 194 and an internal surface 193. Mixing vessel 190 comprising a cylindrical mixing chamber may be lined and/or comprised of a corrosion resistant and temperature transfer resistant material. In some embodiments, the core of mixing vessel 190 comprising a cylindrical mixing chamber may comprise stainless steel. The size and height of the walls of mixing vessel 190 comprising a cylindrical mixing chamber may be designed to maintain sorbent 20 in a dilute phase. The shape of mixing vessel 190 comprising a cylindrical mixing chamber may be designed to allow for turbulence formation or turbulent flow in the cylindrical vessel 190 following in flow of sorbent 20 and compressed air 60 through first end 191 via inlet 31.

Mixing vessel 190 comprising a cylindrical mixing chamber may have one or more atomizers 130 disposed thereon. Atomizer 130 may be operable to allow atomization of impregnant 100 to form atomized droplets of impregnant 100. Atomized 130 may be also operable to allow inflow of atomized droplets. Mixing vessel 190 comprising a cylindrical mixing chamber may be operable to allow inflow and mixing of sorbent 20 and atomized droplets of impregnant 100 to form impregnated sorbent 165 also referred to as product 165. Product discharge tube 140 (also called outlet 140) may be disposed on flange 196 at second end 191 of mixing vessel 190 comprising a cylindrical mixing chamber.

In some embodiments, mixing vessel 190 comprising a cylindrical mixing chamber is designed to generate a turbulence formation having flow and dynamics for efficient mixing of milled or non-milled sorbent 20 with atomized droplets of impregnant 100. In some embodiments, construction of mixing vessel 190 comprising a cylindrical mixing chamber with temperature transfer resistant material may be designed to facilitate maintenance of the temperature of a reaction in cylinder 190 within a range where impregnant 100 (e.g., aqueous impregnant) remains in an aqueous phase and is not converted into a gaseous phase.

Mixing vessel 190 comprising a cylindrical mixing chamber may also be designed to have a reverse flow for discharging impregnated sorbent 165 via product discharge tube 140 out of the cylinder 190. The shape of mixing vessel 190 comprising a cylindrical mixing chamber may be operable to reduce or prevent caking and plugging of outlets and inlets by components of the reaction or by product. In some embodiments, maintenance of turbulent velocity during formation and drafting of impregnant sorbent 165 may reduce or prevent caking or plugging. Additional details regarding mixing vessel 190 comprising a cylindrical mixing chamber are described in FIG. 4.

In apparatus 10, delivery of sorbent 20 into first end 191 of mixing vessel 190 comprising a cylindrical mixing chamber via inlet 31 may be facilitated by eductor 40. Apparatus 10 may comprise compressed air source 70 having compressed air 60 operable to be delivered with sorbent 20 into bottom end 59 of mixing vessel 50 having a conical mixing chamber via regulator 81, pressure valve 91, valve 80, element 85. In some embodiments a rotary valve and a tee may be used for conveying dilute phase sorbent. In some embodiments, pump 40 may be used. Compressed air source 70 may in non-limiting embodiments comprise an air cylinder having air under pressure, a source having air under low pressure or an air blower.

Container 101 may contain impregnant 100 and may be operable to deliver or feed sorbent 20 via pump 110 into atomizers 130. Rotameter 120 may be connected to pressure valve 94 and element 96 operable to regulate inflow of impregnant 100 into atomizers 130.

Compressed air source 70 may be designed to supply compressed air 60 to one or more atomizers 130 located at one or more locations on the surface of mixing vessel 190 comprising a cylindrical mixing chamber via inlets 32. Regulator 82 may control the flow of compressed air to atomizers 130. Pressure valve 93 and air flow meter 85 may regulate the flow of compressed air 60.

FIG. 3 depicts four atomizers 130. However, teachings recognize that apparatus 10 is not limited to the number of atomizers or the location of atomizers. More or fewer atomizers 130 may be present and may be located at several locations on the surface of mixing vessel 190 comprising a cylindrical mixing chamber (although not expressly depicted). In some embodiments, atomizer 130 may be operable to atomize impregnant 100 into atomized droplets that are similar in size to the size of milled sorbent 20. In some embodiments, atomizer 130 may be operable to atomize impregnant 100 into atomized droplets having a size range of, but not limited to, from about 10μ to about 30μ.

Atomizer 130 may be designed to spray atomized droplets of aqueous impregnant at an angle relative to the turbulent flow of sorbent 20. The angle of spray of atomizer 130 may be broad enough to distribute impregnant 100 to substantially all particles of sorbent 20. The angle of the atomizer spray may also be designed to avoid spraying the exiting product 165.

An impregnated sorbent 165, or product 165, may exit mixing vessel 190 comprising a cylindrical mixing chamber through product discharge tube 140. Regulatory valve 80 may control the flow of product 165 into collection chamber 160. 152 may be a temperature indicator to measure the temperature of exiting impregnated sorbent 165 and air in dilute phase.

Product discharge tube 140 may be attached to collection chamber 160 (also referred to as dust collector 160) wherein impregnated milled sorbent 165 may be collected following impregnation in mixing vessel 190 comprising a cylindrical mixing chamber. Dust collector 160 may be similar to that described in sections above and may comprise elements such as but not limited to filters, blower, and/or a bottom hopper. Rotary valve 170 may control the flow of impregnated sorbent 165 into chamber 180.

Automated and manual controls of apparatus 10 shown in FIG. 3 may be similar to those described for apparatus 10 of FIG. 1.

In an exemplary embodiment, sorbent 20 flows through apparatus 10 of FIG. 3 to form an impregnated sorbent 165 in mixing vessel 190 comprising a cylindrical mixing chamber. In some embodiments, sorbent 20 may be a milled sorbent. Teachings recognize that any sorbent, milled, powdered or un-milled sorbent may be used in conjunction with apparatus 10 of FIG. 3 and the apparatus and/or apparatus design does not limit the usage of a particular sorbent type. In one example embodiment, flow of sorbent 20, through apparatus 10, may begin with delivery of sorbent 20 from sorbent delivery chamber 30 into first end 191 of mixing vessel 190 comprising a cylindrical mixing chamber via inlet 31. Delivery and flow of sorbent 20 into mixing vessel 190 comprising a cylindrical mixing chamber may be facilitated by compressed air source 70 having compressed air 60. Accordingly, compressed air 60 and sorbent 20 may be delivered (or fed) simultaneously into first end 191 of mixing vessel 190 comprising a cylindrical mixing chamber via inlet 31 located on first end 191 and may be regulated by one or more of regulator 81, pressure valve 91, valve 80, and/or element 85 through eductor 40. Sorbent 20 with air 60 may comprise a dilute phase sorbent. In some embodiments, sorbent 20 may enter end 59 of mixing vessel 190 comprising a cylindrical mixing chamber at a rate of from about 1000 lb/hr to about 5000 lb/hr.

Inflow of sorbent 20 with compressed air 60 into the cylindrical chamber mixing vessel 190 comprising a cylindrical mixing chamber may result in a turbulence formation or a turbulent flow comprising particles of sorbent 20 having a turbulent velocity. At the same time, impregnant 100 may be delivered into the cylindrical chamber of mixing vessel 190 comprising a cylindrical mixing chamber via atomizers 130. Delivery of impregnant 100 from container 101 into atomizers 130 may be facilitated by pump 110, pressure valves 94 and 95, element 96, and rotameter 120. Compressed air 60 from compressed air source 70 may be delivered into atomizers 130 simultaneously as impregnant 100. Compressed air 60 along with impregnant 100 enters an atomizer 130 and may be atomized into atomized droplets of impregnant 100 which may be sprayed onto the turbulent flow of sorbent and compressed air in mixing vessel 190 comprising a cylindrical mixing chamber.

In some embodiments a finer particle size of atomized droplets of impregnant 100 formed by atomizer 130 may result in a larger surface area of impregnant 100 operable to contact sorbent 20. In some embodiments, atomizer 130 may spray atomized droplets of impregnant 100 at an angle relative to the turbulent flow of sorbent 20. In some embodiments, the angle of spray of atomizer 130 may distribute impregnant to substantially all particles of sorbent 20. In some embodiments, multiple atomizers maximize the contact and mixing of sorbent 20 with impregnant 100.

As atomized droplets of impregnant 100 flow in through atomizers 130 into cylinder 190, impregnant 100 comes in contact with a turbulent formation comprising milled sorbent 20 and compressed air 60. This results in mixing sorbent 20 and impregnant 100 in cylinder 190. In some embodiments, the mixing may be turbulent mixing (i.e., mixing occurring at turbulent velocities of one or more of the components being mixed). Mixing results in adsorption of impregnant 100 into milled sorbent 20 and formation of impregnated sorbent 165.

In some embodiments, turbulence formation in mixing vessel 190 comprising a cylindrical mixing chamber may have flow and dynamics for efficient mixing of sorbent 20 with atomized droplets of impregnant 100. In embodiments where non-milled sorbents 20 may be impregnated using cylinder 190 and/or other parts of apparatus 10, particle size of non-milled sorbent 20 may be fine enough to fluidize with compressed air 60 at a respective velocity of turbulence to allow mixing of non-milled sorbent particles 20 with impregnant 100.

Impregnated sorbent 165 may exit mixing vessel 190 comprising a cylindrical mixing chamber by a reverse flow via product discharge tube 140. Product 165 may exit by drafting of discharge tube 140.

Figure 4:
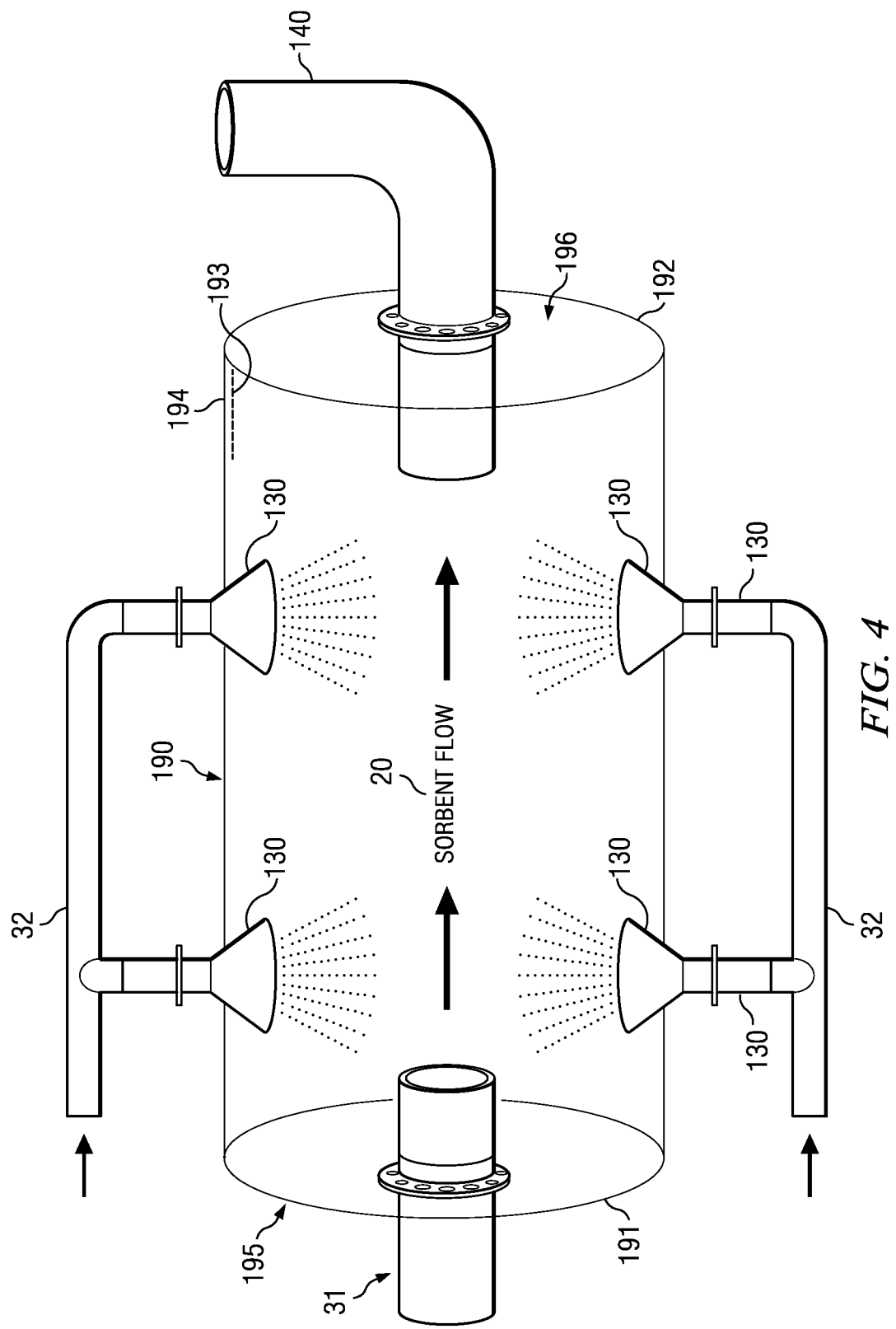
FIG. 4 illustrates a mixing vessel having a cylindrical mixing chamber, according to one example embodiment.

FIG. 4 depicts a three-dimensional view of mixing vessel 190 comprising a cylindrical mixing chamber. Mixing vessel 190 comprising a cylindrical mixing chamber is a cylindrical chamber having a first end 191 and a second end 192. A first flange 195 may be disposed on first end 191. Flange 195 may have inlet 31 for entry of sorbent 20 and compressed air 60 into cylinder 190.

One or more atomizers 130 may be disposed on the surface of mixing vessel 190 comprising a cylindrical mixing chamber at various locations as described earlier. Impregnant 100 and compressed air 60 may enter atomizer 130 through inlets 32 located toward outer surface 194 of mixing vessel 190 comprising a cylindrical mixing chamber. Atomized droplets of impregnant 100 may enter mixing vessel 190 comprising a cylindrical mixing chamber through atomizer 130 toward inner surface 193.

Mixing vessel 190 comprising a cylindrical mixing chamber may have a second flange 196 located on second end 192. Product discharge tube 140 may be disposed in second flange 196 of mixing vessel 190 comprising a cylindrical mixing chamber.

In some embodiments, the shape of mixing vessel 190 comprising a cylindrical mixing chamber may be designed to allow for turbulence formation in cylinder 190 following flow of sorbent 20 and compressed air 60 through inlet 31.

In some embodiments, mixing vessel 190 comprising a cylindrical mixing chamber is designed to generate a turbulence formation having flow and dynamics for efficient mixing of milled sorbent 20 with atomized droplets of impregnant 100. In embodiments where non-milled sorbents may be impregnated using cylinder 190 and/or other parts of apparatus 10, the particle size of non-milled sorbent 20 may be fine enough to fluidize with compressed air 60 at a respective velocity of turbulence to allow mixing of non-milled sorbent particles 20 with impregnant 100.

In some embodiments, mixing vessel 190 comprising a cylindrical mixing chamber may be designed to control the temperature of a reaction. In some embodiments, the temperature of components in cylinder 190 may be maintained within a range where impregnant 100 remains in an aqueous phase and is not converted into a gaseous phase.

Apparatus 10 of the disclosure as shown in FIGS. 1-4 may, in some embodiments, be designed to generate turbulence when the ratio of the inertial force of a fluid stream (e.g., of sorbent 20 and compressed air 60) to its viscous force exceeds a critical value. In some embodiments, apparatus design of the present disclosure may result in an increased residence time, which is the time of contact between an impregnant 100 and a sorbent 20. An increased residence time may a facilitate distribution of an impregnant 100 uniformly across the particles of a sorbent 20 allowing for increased adsorption.

In some embodiments, apparatus 10 of the disclosure may be designed to produce turbulence and residence times that allow for uniform distribution of impregnant 100 across sorbent 20 to allow sufficient time for the moisture in an impregnant 100 (e.g., aqueous impregnant such as a halogen solution) to be either adsorbed onto pores of a sorbent and/or evaporate such that it does not condense on the surface of an impregnant sorbent 165.

Apparatus 10 as shown in FIG. 1 and FIG. 3 as well as embodiment devices shown in FIGS. 2A-2G and FIG. 4 may be used to make compositions of the disclosure in accordance methods of the disclosure. The present disclosure provides several methods to make an impregnant sorbent 165.

Figure 5A:
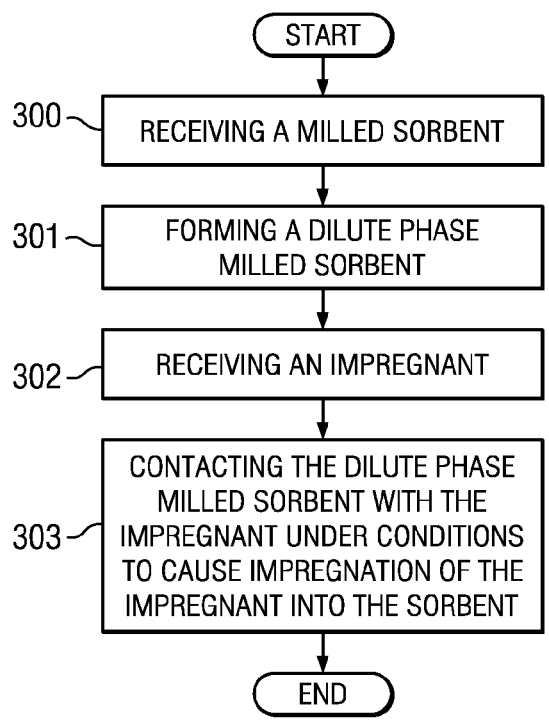
FIG. 5A illustrates an exemplary method for impregnating a milled sorbent, according to one example embodiment.

Some exemplary methods of the disclosure relate to impregnating a milled (or powdered) sorbent. One such exemplary method is illustrated in FIG. 5 and begins at step 300 when a milled sorbent is received. At step 301, milled sorbent is formed into a dilute phase milled sorbent. This may comprise mixing milled sorbent with a gas, such as air, to a conveying velocity that exceeds the saltation velocity of the sorbent. Step 302 comprises receiving an impregnant, and step 303 comprises contacting the dilute phase milled sorbent with the impregnant under conditions to cause impregnation of the impregnant into the milled sorbent.

In some embodiments, a method as described above may be performed in apparatus 10 of the disclosure comprising a mixing vessel 50 having a conical mixing chamber or an mixing vessel 190 comprising a cylindrical mixing chamber. In some embodiments, the particle size of a milled sorbent may be similar to the particle size of an impregnant during the contacting step.

Exemplary conditions under which impregnation may occur may include one or more of the following: atomizing an impregnant to form atomized impregnant droplets; generating a turbulent velocity of dilute phase milled sorbent; contacting atomized impregnant and dilute phase milled sorbent by spraying atomized droplets of impregnant into a turbulent flow of dilute phase milled sorbent; turbulently mixing atomized impregnant and dilute phase sorbent; and/or controlling temperature of the mixing; synchronization of spraying by atomizer and turbulent flow of sorbent; and/or preventing spraying by atomizer onto formed product.

In some embodiments, an atomized impregnant may be an aqueous impregnant. Accordingly, in some embodiments of the method, a liquid phase (aqueous impregnant) may be mixed with a fluid phase comprising dilute phase sorbent at a turbulent velocity. In one embodiment, where an aqueous impregnant may be used, a condition may comprise maintaining or controlling the temperature to avoid evaporation of liquid from the aqueous sorbent.

In some embodiments, a non-aqueous impregnant may be used. In such embodiments, a gas phase impregnant may be mixed with a liquid phase (or dilute phase) milled sorbent.

Figure 5B:
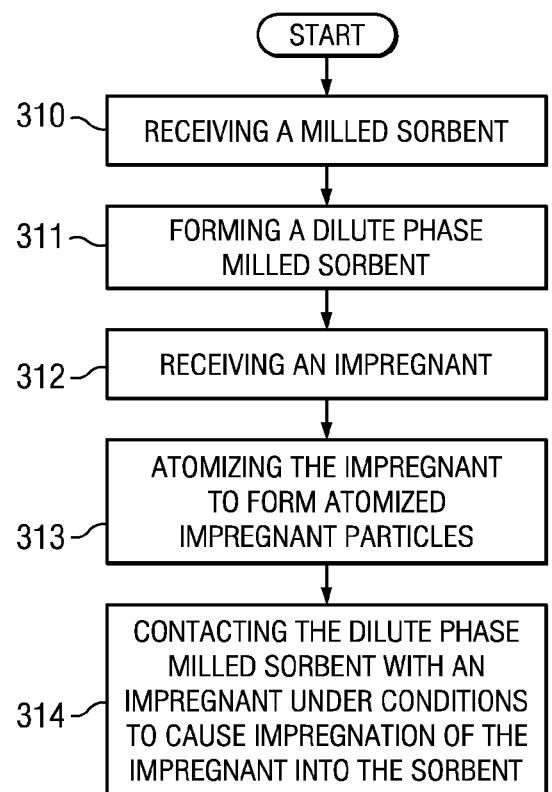
FIG. 5B illustrates an exemplary method for impregnating a milled sorbent, according to one example embodiment.

Another method of the disclosure operable to impregnate a milled or powdered sorbent is illustrated in FIG. 5B and starts with step 310 when a milled sorbent is received. At step 311, milled sorbent is formed into a dilute phase milled sorbent. Step 312 comprises receiving an impregnant, and step 313 comprises atomizing the impregnant to form atomized impregnant droplets. At step 314, the dilute phase milled sorbent is contacted with the atomized impregnant under conditions to cause impregnation of the impregnant into the milled sorbent.

In some embodiments, a method as described in FIG. 5B may be performed in apparatus 10 of the disclosure comprising mixing vessel 50 having a conical mixing chamber or mixing vessel 190 comprising a cylindrical mixing chamber. In some embodiments, particle size of a milled sorbent may be similar to the particle size of an impregnant during the contacting step.

In the two exemplary methods described above, an example sorbent that may be used may comprise a milled or powdered activated carbon. Powdered activated carbon may currently be the Best Available Control Technology ("BACT") for the removal of mercury, particularly elemental mercury, from the exhaust gases of mercury emitting facilities such as coal-fired power plants. An example impregnant may be a halogen, such as bromine, for the removal of contaminating mercury from flue gases or exhausts from coal power plants. In some embodiments, the halogen may be in an aqueous phase. In other embodiments, the halogen may be a gas.

For applications relating to removal of mercury and/or elemental mercury from coal-fired power plants, other methods have shown significantly better mercury removal using a halogenated activated carbon than with a non-halogenated activated carbon. However, all of these methods involve first halogenating a granular activated carbon followed by milling the halogenated granular carbon to obtain halogenated powdered activated carbon. For example, in some methods, a halogen compound is dissolved in an aqueous solution to impregnate the carbon in its granular form prior to milling it into a powder. In some other methods, sorbents may be impregnated with halogens by spraying granular activated carbon with an aqueous NaBr solution immediately prior to feeding it into a mill where it is ground into powdered activated carbon.

An attempt to impregnate powdered activated carbon with an aqueous halogen solution may involve mixing a halogen solution into powdered activated carbon in batches and then drying the batches. However, these efforts are inefficient, expensive and inconsistent in the composition and quality of product formed.

Accordingly, while sorbents such as granular activated carbon may be impregnated by halogenation, the halogenated granular carbon may be milled later to obtain halogenated powdered activated carbon. Milling an impregnated sorbent is associated with several problems. For example, halogens used for impregnation are corrosive and corrode and damage mill parts. Accordingly, such methods result in repeated replacement of mill parts and downtime of milling operations due to maintenance- and/or repair-related shut downs.

Another problem associated with methods where halogen impregnation is followed by milling of the impregnated sorbent is contamination by halogenated activated carbon. Moving parts of mills used for milling get contaminated with toxic halogens, which render the mill unusable for milling other products. Accordingly, previous methods have imposing limitations of exclusive use of a mill for halogen impregnated sorbents pose drawbacks.

Methods that use milling following impregnation are also plagued with flowability issues. Lines often are caked or plugged by the activated carbon, the impregnant and/or by the impregnant sorbent product which may have poor flowability. This reduces milling capacity.

In contrast, present methods for impregnation of a milled sorbent may be operable to impregnate a large surface area since a milled sorbent has a greater surface area to adsorb/trap in more impregnant. For example, each grain of granular activated carbon may become approximately 472,000 particles of powdered activated carbon. One technical advantage of methods of the present disclosure may be the formation of a product having a higher concentration of impregnant as compared to a product formed by other methods that perform the milling step following halogenation/impregnation. In some embodiments, the present methods may produce impregnated sorbents having substantially higher concentrations of impregnants. In some embodiments, a method of the disclosure may comprise impregnating a sorbent with from about 3% to about 4% of Br.

Use of an atomizer and turbulent flow as described in some embodiments ensures better contact and mixing of a sorbent with an impregnant and results in uniformity of impregnation. Accordingly, in some embodiments, the present methods produce substantially uniformly impregnated sorbent.

Figure 6:
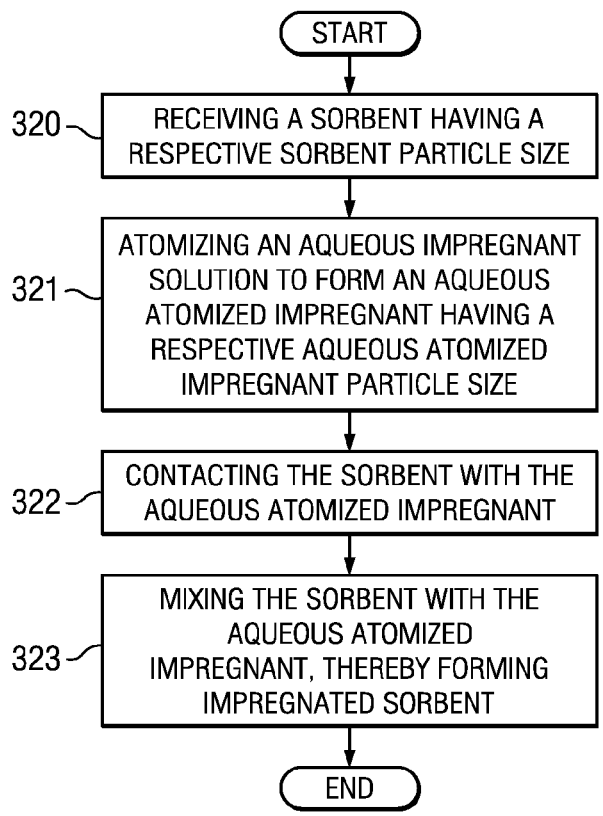
FIG. 6 illustrates an exemplary method for impregnating a sorbent, according to one example embodiment.

In some embodiments, methods of the disclosure relate to impregnation of non-milled sorbents. An exemplary method operable to impregnate an un-milled sorbent is illustrated in FIG. 6 and starts from step 320 where an un-milled sorbent having a respective sorbent particle size is received. The un-milled sorbent may be in a dilute phase. At step 321, an aqueous impregnant solution is atomized to form an aqueous atomized impregnant having a respective aqueous atomized impregnant particle size. Step 322 comprises contacting the sorbent with the aqueous atomized impregnant, and step 323 comprises mixing the sorbent with the aqueous atomized impregnant, thereby forming impregnated sorbent.

In some embodiments, a method as described in FIG. 6 may be performed in apparatus 10 of the disclosure comprising mixing vessel 50 having a conical mixing chamber or mixing vessel 190 comprising a cylindrical mixing chamber. Contacting may comprise generating a turbulent velocity of sorbent particles and spraying impregnant using one or more atomizers. Mixing the sorbent may comprise turbulent mixing.

In some embodiments of this method, the particle size of an un-milled sorbent may be substantially similar to the particle size of aqueous atomized impregnant. In some embodiments, the particle size of an un-milled sorbent may be in the range of from about 10µ to about 30µ, and the size range of an aqueous atomized impregnant droplet size may be from about 10µ to about 30µ. However, the present methods are not limited to these atomized droplet size ranges and other sizes of droplets may be used as well.

Figure 7:
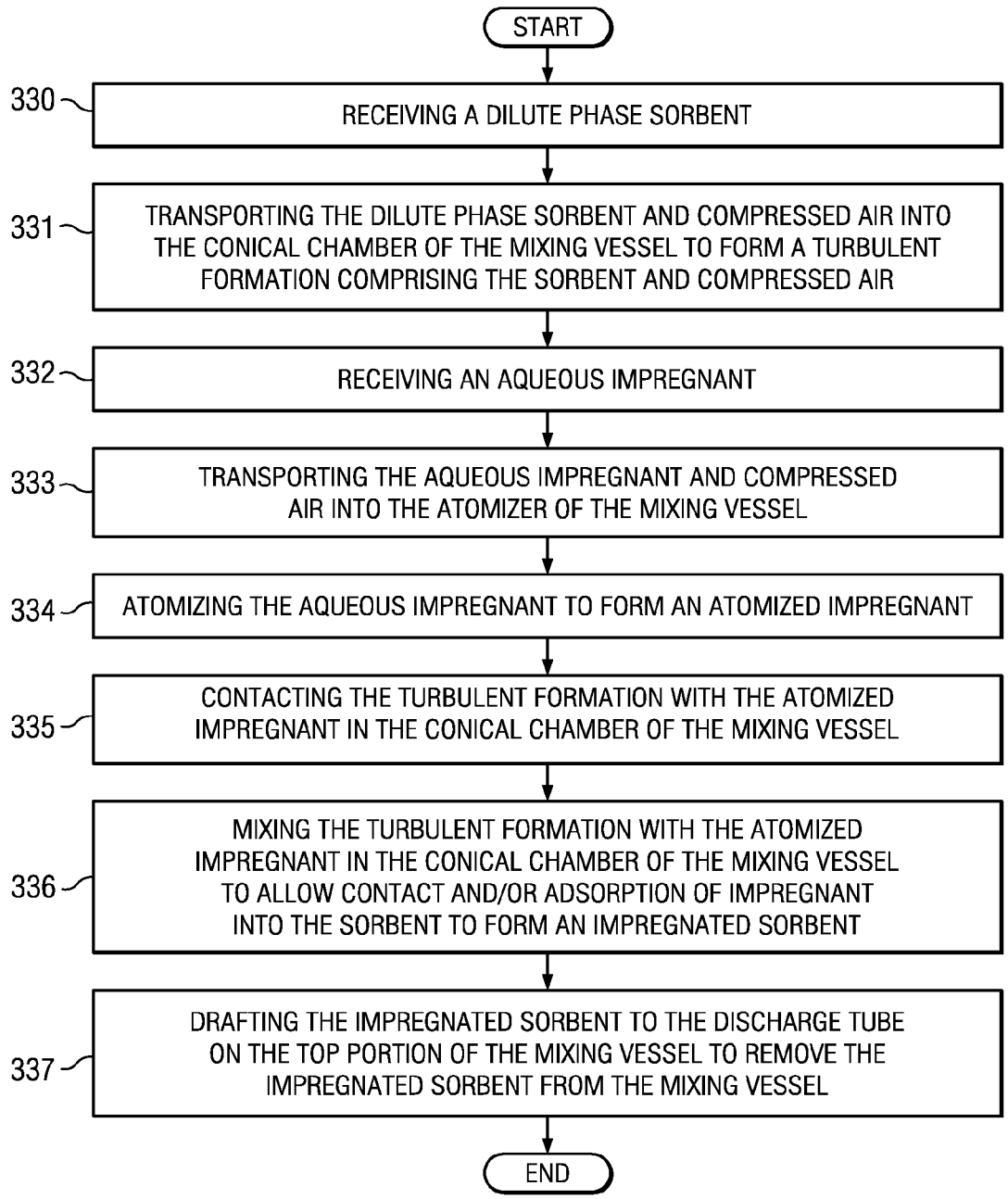
FIG. 7 illustrates an exemplary method for impregnating a sorbent using a mixing vessel having a conical mixing chamber, according to one example embodiment.

In some embodiments, the disclosure relates to methods for making impregnated sorbents using apparatus 10 of the disclosure. FIG. 7 illustrates an exemplary method for impregnating sorbent 20 using mixing vessel 50 having a conical mixing chamber and begins at step 330, which comprises receiving a dilute phase sorbent 20. At step 331, the dilute phase sorbent 20 and compressed air 60 are transporting into the bottom of conical chamber 54 of mixing vessel 50 having a conical mixing chamber to form a turbulent formation comprising sorbent 20 and compressed air 60. At step 332, an aqueous impregnant 100 is received, and at step 333, the aqueous impregnant 100 and compressed air 60 are transported into one or more atomizers 130 located in mixing vessel 50 having a conical mixing chamber. Step 334 comprises atomizing the aqueous impregnant 100 to form an atomized impregnant. Step 335 comprises contacting the turbulent formation with the atomized impregnant in the conical chamber 54 of mixing vessel 50 having a conical mixing chamber. Step 336 comprises mixing the turbulent formation with the atomized impregnant in conical chamber 54 of mixing vessel 50 having a conical mixing chamber to allow adsorption of impregnant 100 into sorbent 20 to form impregnated sorbent 165. Mixing may comprise contacting the surface of sorbent with impregnant. Mixing may in some embodiments comprise adsorption of impregnant 100 into sorbent. Step 337 comprises drafting impregnated sorbent 165 to discharge tube 140 on top portion 58 of mixing vessel 50 having a conical mixing chamber to remove impregnated sorbent 165 from a mixing vessel having a conical mixing chamber 50.

In some embodiments, a turbulent formation may comprise sorbent 20 and compressed air 60. In some embodiments, a turbulent formation may comprise sorbent 20, atomized impregnant, and compressed air 60. Turbulence formation used for mixing a milled sorbent 20 with an impregnant 100 may be referred to as turbulent mixing.

Figure 8:
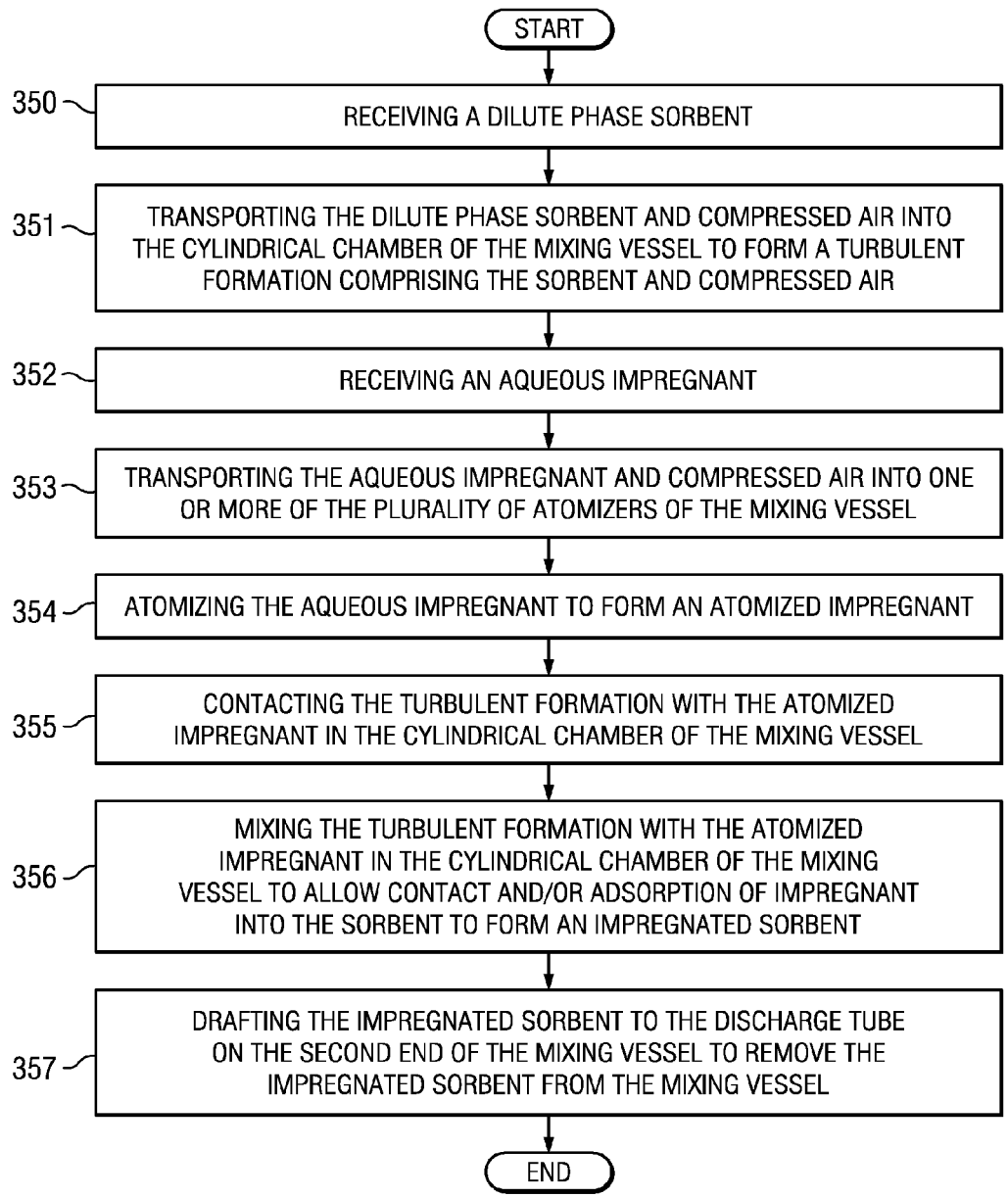
FIG. 8 illustrates an exemplary method for impregnating a sorbent using a mixing vessel having a cylindrical mixing chamber, according to one example embodiment.

In some embodiments, a method of the disclosure may use a mixing vessel having a cylindrical mixing chamber 195 as described in FIGS. 3 and 4. FIG. 8 illustrates an example method and starts at step 350 where a dilute phase sorbent 20 is received. In step 351, dilute phase sorbent 20 and compressed air 60 are transported into a cylindrical chamber of mixing vessel 190 comprising a cylindrical mixing chamber to form a turbulent formation comprising sorbent 20 and compressed air 60. Step 352 comprises receiving an aqueous impregnant 100, and step 353 comprises transporting the aqueous impregnant 100 and compressed air 60 into one or more of the plurality of atomizers 130 of mixing vessel 190 comprising a cylindrical mixing chamber. Step 354 comprises atomizing the aqueous impregnant 100 to form an atomized impregnant, and step 355 comprises contacting the turbulent formation with the atomized impregnant in cylindrical chamber of mixing vessel 190 comprising a cylindrical mixing chamber. Step 356 comprises mixing the turbulent formation with the atomized impregnant in cylindrical chamber of mixing vessel 190 comprising a cylindrical mixing chamber to allow contact of impregnant into the sorbent to form impregnated sorbent 165. Mixing at step 356 may comprise contacting the surface of sorbent with impregnant. Mixing at step 356 may in some embodiments comprise adsorption of impregnant 100 into sorbent. Step 357 comprises drafting impregnated sorbent 165 to discharge tube 140 on second end 192 of mixing vessel 190 comprising a cylindrical mixing chamber to remove impregnated sorbent 165 from mixing vessel 190 comprising a cylindrical mixing chamber.

Methods of the present disclosure may advantageously result in impregnant sorbents 165 having a higher concentration of impregnant as compared to a product formed by other methods. For example, in embodiments where milled sorbents are impregnated, greater surface area of sorbent is impregnated. In embodiments where non-milled sorbents are impregnated, the use of atomized impregnant solution greatly increases the contact between sorbent and impregnant molecules. In addition, apparatus 10 of the disclosure are designed for turbulent mixing, which greatly enhances contacting and mixing of sorbent and impregnant molecules. Accordingly, methods of the disclosure may produce impregnated sorbents having substantially higher concentrations of impregnants. In some embodiments, a method of the disclosure may comprise increasing Br distribution. In some embodiments, the present methods produce substantially uniformly impregnated sorbent 165. In some embodiments, a method of the disclosure may be a continuous process.

Embodiments of the disclosure also relate to impregnant sorbents produced by methods of the disclosure. Compositions of the disclosure may comprise impregnated sorbents 165 made by a method and/or in an apparatus of the disclosure.

An impregnated sorbent composition 165 of the disclosure may comprise a porous sorbent 20 having one or more inorganic impregnants 100 such as but not limited to a halogen, silver or a cation such as Al, Mn, Zn, Fe, Li, Ca. In some embodiments, a composition of the disclosure may comprise a sorbent comprising an activated carbon and an impregnant comprising a halogen. One example embodiment composition may comprise a powdered activated carbon impregnated with bromine.

In some embodiments, a composition of the disclosure may comprise a sorbent substantially uniformly impregnated with an impregnant. In some embodiments, a composition of the disclosure may comprise a sorbent with a high concentration of impregnant per unit of sorbent. Additionally, a composition of the disclosure may have a more uniform distribution of impregnant as compared to an impregnated sorbent made by other methods. One technical advantage of an impregnant of the disclosure may be an improved sorbent efficiency.

Sorbent efficiency of an impregnated sorbent according to the disclosure, (also referred to herein variously as "adsorption efficiency of a sorbent and/or an impregnated sorbent," "efficiency of sorbent," or "sorbent efficacy") may be the ability of an impregnated sorbent to remove substantially all molecules of a contaminant (e.g., a hazardous molecule) from contaminated fluid (liquid or gas). An impregnated sorbent made by the methods and/or apparatuses of the disclosure may remove a contaminant by adsorbing, binding to, or sequestering a contaminant from a contaminated fluid. In some embodiments, an impregnated sorbent of the disclosure may chemically modify a contaminant which may render a contaminant less toxic. For example, in an example embodiment, an impregnated sorbent comprising a halogen (e.g., bromine (Br)) may oxidize mercury from a flue gas or an exhaust gas thereby decontaminating it.

In some embodiments, sorbent efficiency may be the ability of an impregnated sorbent of the disclosure to remove, reduce, or lower a contaminant from contaminated fluid to a legally acceptable level. In other embodiments, sorbent efficiency may be the ability of an impregnated sorbent to remove a substantial portion of a contaminant from a contaminated fluid. Sorbent efficiency may also represent the ability of an impregnated sorbent to remove from about 20% to about 100% of a contaminant from contaminated fluid. In some embodiments, sorbent efficiency may be the ability of an impregnated sorbent to lower the levels of a contaminant in a contaminated fluid from about 20% to about 99.9%. In some embodiments, sorbent efficiency may be the ability of an impregnated sorbent to lower the levels of a contaminant in a contaminated fluid from about 20% to about 99.9%. In some embodiments, an impregnated sorbent comprising an activated carbon sorbent and a halogen as described herein may have a sorbent efficiency may be the ability to lower the levels of mercury in a contaminated fluid from about 20% to about 99.9%.

An impregnated sorbent of the disclosure may comprise a variety of carbon sorbents and/or non-carbon sorbents. Exemplary non limiting examples of non-carbon adsorbents may include a zeolite (aluminosilicate), a polymeric resin, a non-metallic resin, a clay, and/or an ion exchange resin. The section below describes different sources and types of carbon sorbent materials that may be used to form a composition of the disclosure. However, teachings recognize that impregnant sorbent compositions of the present disclosure are not limited to the described sorbents.

In some embodiments, activated carbon sorbents may be impregnated by apparatuses and methods described herein to arrive at some example compositions of the disclosure. Activated carbons may be used as sorbents to decontaminate hazardous agents or contaminants such as but not limited to hydrogen sulfide ($H_2S$), ammonia ($NH_3$), formaldehyde (HCOH), radioisotopes iodine-131 ($^{131}I$) and mercury (Hg). An activated carbon (also known as activated charcoal or activated coal) may be a powdered, granular, briquetted and/or pelleted form of an amorphous carbon and is generally characterized by a large surface area per unit volume due to the presence of numerous fine pores on the surface of the activated carbon. Activated carbons are capable of sequestering gases, liquids, and/or dissolved substances on the surface of its pores primarily by adsorption. Activated carbons have a broad spectrum of adsorptive activity, excellent physical and chemical stability, and ease of production from readily available materials including waste materials. A variety of carbonaceous raw materials may be used for the manufacture of activated carbon including, but not limited to, wood, peat, lignite, coir, bone char made by calcining bones, nut shells (e.g., coconut), coal, petroleum coke and petroleum pitch.

Activation may comprise treating carbon to open many pores having a diameter that ranges from about 1.2 nanometers (nm) to about 20 nm (e.g., gas-adsorbent carbon) or up to about 100 nm-diameter range (e.g., decolorizing carbons). Following activation, an activated carbon may have a large surface area (typically 500-1500 $m^2/g$) rendering it operable to adsorb one or more hazardous agents or contaminants.

A variety of activation methods may be used to activate a carbon. Exemplary non-limiting methods used to activate carbons may comprise subjecting the carbon to selective oxidation using steam, carbon dioxide, flue gas, or air to open the pore structure. Other methods of activation may include mixing chemicals, such as metal chlorides (e.g., zinc chloride), metal sulfides, metal phosphates, potassium sulfide, potassium thiocyanate, and/or phosphoric acid with a carbonaceous matter followed by calcining and washing the residue. In addition to high surface area, certain chemical treatments may be used enhance the absorbing properties of activated carbon sorbents. Teachings of the present disclosure recognize that the present embodiments are not limited to any particular methods of activation or to any particular raw material sources and/or formulations of activated carbon sorbents.

Under an electron microscope, high surface-area structures of activated carbon reveal intensely convoluted individual particles displaying various kinds of porosity. Micropores are seen as areas where flat surfaces of graphite-like material run parallel to each other, separated by only a few nanometers. Micropores may provide superior conditions for adsorption since adsorbing material can interact with many surfaces simultaneously. Activated carbon may bind or adsorb materials (such as a contaminant) by van der Waals force or London dispersion force. In some instances activated carbons may bind or adsorb certain contaminant materials by chemosorption.

Activated carbons are complex products which are difficult to classify on the basis of their behavior, surface characteristics and preparation methods. However, some example activated carbons classified broadly based on their physical characteristics that may be used as sorbents in non-limiting embodiments of the present disclosure may include: powdered activated carbon (PAC), granular activated carbon (GAC), extruded activated carbons (EAC), impregnated carbons, and polymer coated carbons. Some embodiments of the disclosure may use activated carbon aerogels having even higher surface areas as sorbents for some applications.

Exemplary PAC's may comprise active carbons as powders or fine granules less than 1.0 millimeters (mm) in size with an average diameter between 0.15 mm and 0.25 mm. PAC's may have a large surface to volume ratio with a small diffusion distance. PAC may comprise crushed or ground carbon particles, 95-100% of which are passed through a designated mesh sieve.

GAC's have a relatively larger particle size compared to PAC and therefore may have a smaller external surface. GAC's may function via adsorbate diffusion and may be used for adsorption of gases and vapors as their rate of diffusion are faster. Granulated carbons may be used for water treatment, deodorisation and separation of components of flow system. GAC may be either in granular form or extruded. GAC are typically designated by sizes such as 8×20, 20×40, or 8×30 for liquid phase applications and 4×6, 4×8 or 4×10 for vapor phase applications. A 20×40 carbon is made of particles that pass through a U.S. Standard Mesh Size Number 20 sieve (0.84 mm) (generally specified as 85% passing), but are retained on a U.S. Standard Mesh Size Number 40 sieve (0.42 mm) (generally specified as 95% retained). American Water Works Association (AWWA) (1992) B604 uses the 50-mesh sieve (0.297 mm) as the minimum GAC size.

A GAC may comprise activated carbon retained on a 50-mesh sieve (0.297 mm) and PAC material as finer material, while The American Society for Testing and Materials (ASTM) classifies particle sizes corresponding to an 80-mesh sieve (0.177 mm) and smaller as PAC.

An EAC may comprise a combination of a PAC with a binder, fused together and extruded into a cylindrical shaped activated carbon block having diameters from 0.8 mm to 130 mm. EAC's may be used for gas phase applications because of their low pressure drop, high mechanical strength and low dust content.

Polymer coated carbon may comprise a porous carbon coated with a biocompatible polymer to give a smooth and permeable coat without blocking the pores. The resulting activated carbon may be useful for hemoperfusion. Hemoperfusion is a treatment technique in which large volumes of the patient's blood are passed over an adsorbent substance in order to remove toxic substances from the blood.

Some embodiments relate to compositions of the disclosure comprising an activated carbon sorbent that may be milled.

Although several embodiments have been illustrated and described in detail, it will be recognized that substitutions and alterations are possible without departing from the spirit and scope of the present disclosure, as defined by the appended claims.

What is claimed is:

1. An apparatus for impregnating a sorbent, comprising:
 a mixing vessel having at least one atomizer, the mixing vessel operable to facilitate synchronized spraying of atomized impregnant droplets from the atomizer and facilitate synchronized turbulence formation of sorbent particles and atomized impregnant droplets and further operable to facilitate mixing of turbulence formation to form an impregnated sorbent, the mixing vessel having a first end and a second end and further comprising:
 a cylindrical chamber disposed toward the first end;
 a conical chamber disposed toward the second end;
 a top flange disposed toward the first end and having the at least one atomizer disposed thereon, wherein the at least one atomizer is operably coupled to an aqueous impregnant source and a compressed air source and the atomizer operable to atomize the aqueous impregnant into atomized droplets of impregnant;
 a bottom flange disposed toward the second end and having an inlet operable to facilitate inflow of a sorbent and compressed air into the conical chamber; and
 a product discharge tube disposed on the top flange, wherein the conical chamber is operable to facilitate turbulence formation comprising the sorbent and compressed air following inflow of the sorbent and compressed air through the inlet on the bottom flange and the product discharge tube is operable to discharge the impregnated sorbet to an exterior product collector.

2. The apparatus of claim 1, wherein the mixing vessel is comprised of a corrosion resistant material.

3. The apparatus of claim 1, wherein the mixing vessel is comprised of a temperature transfer resistant material.

4. The apparatus of claim 1, wherein the mixing vessel is further operable to maintain the temperature during mixing of turbulence formation and atomize impregnant droplets to form the impregnated sorbent within a range where atomized impregnant droplets remains in an aqueous phase and are not converted into a gaseous phase.

5. The apparatus of claim 1, wherein an angle of spray of the atomizer may be from 10° to 15°.

* * * * *